US006915157B2

(12) United States Patent
Bennett et al.

(10) Patent No.: US 6,915,157 B2
(45) Date of Patent: Jul. 5, 2005

(54) IMPLANTABLE MEDICAL DEVICE FOR ASSESSING HEART FAILURE STATE FROM MECHANICAL PULSUS ALTERNANS

(75) Inventors: Tommy D. Bennett, Shoreview, MN (US); Lawrence J. Mulligan, Andover, MN (US); Edwin G. Duffin, North Oaks, MN (US); Robert C. Hamlen, Edina, MN (US); Wael Abo-Auda, Harriman, TN (US)

(73) Assignee: Medtronic, Inc., Minneapolis, MN (US)

( * ) Notice: Subject to any disclaimer, the term of this patent is extended or adjusted under 35 U.S.C. 154(b) by 194 days.

(21) Appl. No.: 10/368,278

(22) Filed: Feb. 18, 2003

(65) Prior Publication Data

US 2004/0162497 A1 Aug. 19, 2004

(51) Int. Cl.[7] ................................................. A61B 5/04
(52) U.S. Cl. ..................................................... 600/513
(58) Field of Search ............................... 600/300, 513, 600/517; 607/9

(56) References Cited

U.S. PATENT DOCUMENTS

| | | | |
|---|---|---|---|
| 4,291,699 A | 9/1981 | Geddes et al. | |
| 4,802,491 A | 2/1989 | Cohen et al. | |
| 5,265,617 A | 11/1993 | Verrier et al. | |
| 5,368,040 A | 11/1994 | Carney | |
| 5,564,434 A | 10/1996 | Halperin et al. | |
| 5,713,367 A | 2/1998 | Arnold et al. | 128/704 |
| 5,749,900 A | 5/1998 | Schroeppel et al. | |
| 5,904,708 A | 5/1999 | Goedeke | |
| 5,919,210 A | 7/1999 | Lurie et al. | |
| 5,921,940 A | 7/1999 | Verrier et al. | 600/518 |
| 6,224,553 B1 | 5/2001 | Nevo | |
| 6,253,107 B1 | 6/2001 | Albrecht et al. | |
| 6,272,377 B1 | 8/2001 | Sweeney et al. | |
| 6,275,727 B1 | 8/2001 | Hopper et al. | |
| 6,280,409 B1 | 8/2001 | Stone et al. | |
| 6,438,408 B1 | 8/2002 | Mulligan et al. | |
| 6,454,707 B1 * | 9/2002 | Casscells et al. | 600/300 |

OTHER PUBLICATIONS

Euler, David E. et al., "Sympathetic Influences on Electrical and Mechanical Alternans in the Canine Heart," Abstract, *Cardiovascular Research*, vol. 32, No. 5, p. 854–860 (1996).

Rosenbaum, et al., "Predicting Sudden Cardiac Death from T Wave Alternans of the Surface Electrocariogram: Promise and Pitfalls", *Journal of Cardiovascular Electrophysiology*, vol. 7, No. 11, Nov. 1996, pp. 1095–1111.

Hunt, et al., "ACC/AHA Guidelines for the Evaluation and Management of Chronic Heart Failure in the Adult", *ACC/AHA Practice Guidelines*, 2001, pp. 1–37.

Kodama, et al., "Mechanical Alternans in Patients with Chronic Heart Failure", *Journal of Cardiac Failure*, vol. 7, No. 2, 2001, pp. 138–145.

(Continued)

*Primary Examiner*—George Manuel
(74) *Attorney, Agent, or Firm*—Michael C. Soldner; Girma Wolde-Michael (57) ABSTRACT

An implantable heart monitor (IHM) implanted in a patient's body having electrogram (EGM) sense electrodes coupled with EGM sense circuitry to generate sense events upon detection of cardiac depolarizations and a blood pressure measurement transducer disposed in a heart chamber and coupled with blood pressure measurement circuitry operates to assess heart failure state as a function of mechanical pulsus alternans (MPA). MPA episodes are detected, and MPA characteristics of the MPA episode are used alone or as a group as a diagnostic marker of HF state. The MPA episode data set can be stored in memory associated with a time and date stamp. The MPA characteristics of each MPA data set in a series of MPA data sets collected over time can be compared or plotted to determine if a trend indicative of change in HF state is discernible.

30 Claims, 5 Drawing Sheets

OTHER PUBLICATIONS

Kodama, et al., "Changes in the Occurrence of Mechanical Alternans After Long–Term Blocker Therapy in Patients with Chronic Heart Failure", *Japanese Circulation Journal*, vol. 65, Aug. 2001, pp. 711–716.

Surawics, et al., "Cardiac Alternans: Diverse Mechanisms and Clinical Manifestations", *JACC*, vol. 20, No. 2, Aug. 1992, pp. 483–499.

Freeman, et al., "An Evaluation of Pulsus Alternans in Closed–Chest Dogs", *The American Physiological Society*, 1992, pp. H278–H284.

Armoundas, et al., "Pathophysiological Basis and Clinical Application of T–Wave Alternans", *JACC*, vol. 40, No. 2, 2002, pp. 207–271.

Clancy, et al., "A Simple Electrical–Mechanical Model of the Heart Applied to the Study of Electrical–Mechanical Alternans", *IEEE Transactions on Biomedical Engineering*, vol. 38, No. 6, Jun. 1991, pp. 551–560.

Leder, et al., "Alternans of Blood Pressure and Heart Rate in Dilated Cariomyopathy", *PACE*, vol. 25, No. 9, pp. 1307–1314.

* cited by examiner

IMPLANTABLE MEDICAL DEVICE FOR ASSESSING HEART FAILURE STATE FROM MECHANICAL PULSUS ALTERNANS

FIELD OF THE INVENTION

The present invention relates generally to implantable medical devices (IMDs) for monitoring mechanical heart function of a patient's heart, detecting episodes of Mechanical Pulsus Alternans (MPA) and associated episode data, and providing an assessment of the state or progression of heart failure that can be employed diagnostically or in combination with a therapy delivery system for delivering an appropriate therapy.

BACKGROUND OF THE INVENTION

The term "heart failure" (HF) as used herein embraces congestive heart failure and/or chronic heart failure as defined by the American College of Cardiology and the American Heart Association as set forth in a report of the American College of Cardiology/American Heart Association Task Force on Practice Guidelines (Committee to revise the 1995 Guidelines for the Evaluation and Management of Heart Failure) authored by Hunt et al. (ACC/AHA guidelines for the evaluation and management of chronic heart failure in the adult: executive summary, *J Am Coll Cardiol* 2001; 38(7):2101–2113).

Many HF patients exhibit mechanical pulse alternans (MPA), which is a phenomenon wherein alternating mechanical contractions of the heart exhibit alternating values of contraction force or magnitude that cause ejected blood to exhibit like alternating values of diastolic pressure amplitude. MPA has historically be described for the systemic arterial system where alternating high and low arterial pulse pressures have been identified as being related to alternating strengths of contraction (and the resulting stroke volume) of the left ventricle. Similar observations have been described for the pulmonary artery pressure as an indicator of alternating contractile strengths of the right ventricle. MPA has been discussed in the context of increasing heart rate and has been attributed to various functional properties of the heart. See for example: Kodama et al., "Mechanical Alternans in Patients with Chronic Heart Failure", *J Card Fail* 2001; 7(2):138–145; Kodama et al., "Changes in the Occurrence of Mechanical Alternans after Long-term Beta-blocker Therapy in Patients with Chronic Heart Failure. *Jpn Circ J* 2001; 65(8):711–716; and Surawicz et al., "Cardiac Alternans: Diverse Mechanisms and Clinical Manifestations", *J Am Coll Cardiol* 1992; 20(2):483–499.

One potential explanation is based on alternate loading conditions of the left ventricle. If the left ventricle contracts strongly and empties well, then the volume of blood left in the left ventricle, i.e., the end systolic volume (ESV), will be nominal. If the heart rate is relatively low, the left ventricle will refill with blood from the left atrium during the next filling phase resulting in a relatively large end diastolic volume (EDV). This larger EDV will, according to Starling's Law of the Heart, cause the left ventricle to more forcefully contract, thereby emptying the left ventricle and resulting in a lower ESV and a relatively large arterial pulse pressure. Then, normal filling added to a lower ESV will result in a lower EDV. The lower EDV on this beat will result in a weaker contraction (by Starling's Law) and less ejection on the next beat resulting in a lower arterial pulse pressure, a larger ESV and the cycle repeats.

Another explanation is that calcium uptake by the sarcoplasmic reticulum is impaired, resulting in less calcium available for the next cardiac cycle. This has been shown in the only animal model of controlled MPA. See Freeman et al, "An Evaluation of Pulsus Alternans in Closed-chest Dogs", Am *J Physiol* 1992, 262(1 Pt 2):H278–H284. These observations were made in animals where the preload was lowered using an occluder on the vena cava while the heart rate was maintained at 200 bpm. Importantly, preload is decreasing in this setting while MPA increases. This does not rule out volume changes as important determinants of MPA in patients but does suggest that the alterations in calcium handling may be more crucial to the development of MPA.

Alternate descriptions of MPA are based on other cyclic properties of the cellular mechanisms in the myocardial cells. These mechanisms transfer calcium to and from intracellular storage and release sites and are responsible for the contraction and relaxation of the myocyte. If more Ca++ were available for release, it is expected that the contractile force developed would be greater. The normal cellular Ca++ cycling processes are disrupted by disease, such as HF, and the disrupted processes result in cyclic variations that can be exaggerated, producing hemodynamic variants such as MPA.

Although current pacing systems, incorporated into a pacemaker, e.g., the MEDTRONIC® InSync® Model 8040 pacemaker IPG, or into an ICD IPG, e.g., the MEDTRONIC® InSync® Model 7272 ICD IPG, that provide right and left heart pacing to alleviate HF symptoms collect limited amounts of heart rate data (as well as tachyarrhythmia episode data in the case of ICD IPGs), such data does not always provide sufficient information to assess whether the HF symptoms are being alleviated or are worsening. Nor, do such IPGs presently have the capability of measuring mechanical heart function including MPA and formulating and delivering an appropriate therapy based upon the measured mechanical heart function.

HF patient's hearts frequently exhibit MPA but do not exhibit an abnormal EGM or electrical instability that comprises or is a precurser to a tachyarrhythmia. Hearts of patients that are susceptible to tachyarrhythmia episodes exhibit electrical malfunctions that cause mechanical malfunctions. Malignant tachyarrhythmias, including ventricular fibrillation or flutter (VF) or high rate ventricular tachycardia (VT) cause sudden loss of mechanical heart function and cardiac output that can lead to death unless the heart is cardioverted. Consequently, numerous algorithms have been proposed over the years for use in ICDs to identify tachyarrhythmia episodes, typically from measured rate, onset and stability of the measured EGM through sophisticated signal processing techniques.

In this regard, it has long been postulated that a pattern of beat-to-beat alternation in the amplitude or polarity of the T-wave of the characteristic PQRST complex of the ECG or EGM is indicative of electrical instability and predictive of the susceptibility to tachyarrhythmia as set forth in U.S. Pat. No. 5,265,617, for example. This pattern of alternation, referred to as "electrical alternans" or "T-wave alternans", is not always present, but often emerges under conditions where the patient's heart experiences an increased demand due to an increased level of physical or mental stress. Electrical alternans can often be measured at the body surface as a subtle beat-to-beat change in the repeating pattern of an ECG waveform. An overview of electrical alternans is given by Rosenbaum, Albrecht and Cohen in "Predicting sudden cardiac death from T wave alternans of the surface electrocardiogram: promise and pitfalls", *Journal of Cardiovascular Electrophysiology*, November, 1996, Vol. 7(11), pages 1095–1111.

Thus, episodes of electrical alternans and the heart rates at which the episodes occur have been used to assess patients' risk of developing ventricular arrhythmias. This analysis reflects an alternating pattern of the sequence of electrical depolarization as it spreads through the right and left ventricular chambers. Secondary to this electrical derangement, there may be a variable contraction sequence yielding ventricular and systemic blood pressure alternans patterns similar to MPA even though the myocardial fibers are healthy. Thus, the patient at risk of arrhythmias will exhibit electrical alternans and may or may not exhibit mechanical alternans all because of variation in the propagation paths of the excitatory wavefronts rather than due to impaired myocardial fiber contractility.

It has been asserted in U.S. Pat. No. 6,253,107 that electrical alternans is believed to result from an underlying pattern of alternation in the biochemical processes that drive the functioning of the cardiac muscle. In light of observations of the occasional association of MPA with electrical alternans in hearts susceptible to tachyarrhythmias, it is further asserted that electrical alternans begins to have a measurable effect on the contraction of the muscle cells as the level of electrical alternans increases. An article by Clancy, Smith, and Cohen entitled "A simple electrical-mechanical model of the heart applied to the study of electrical-mechanical alternans", *IEEE Transactions on Biomedical Engineering*, June, 1991, Vol. 38(6), pages 551–60, is asserted in the '107 patent as supporting this theoretical relationship between electrical alternans and MPA. The Clancy et al. article noted evidence showing that a subtle electrical alternans observed in the surface ECG may be correlated with the susceptibility to ventricular fibrillation, and offered evidence that MPA generally accompanies electrical alternans. The article indicated that there exists a regime of combined electrical-mechanical alternans during the transition from a normal rhythm towards a fibrillatory rhythm, that the detected degree of alternation is correlated with the relative instability of the rhythm, and that the electrical alternans and MPA may result from a dispersion in local electrical properties leading to a spatial-temporal alternation in the electrical conduction process. This spatial-temporal alternation in the electrical conduction process of electrical alternans is therefore postulated to be the cause of a corresponding MPA detected in the blood pressure waveforms.

It is also asserted in the '107 patent that a healthy heart exhibits a certain level of heart rate variability (HRV) that is evidenced by slightly varying, beat-to-beat heart rates. It is suggested that certain patient's hearts that are susceptible to tachyarrhythmias at times lack such a normal HRV and may exhibit the electrical alternans and/or an alternation in the measured beat-to-beat blood pressure waveform, referred to as "blood pressure alternans" in the '107 patent. A number of IMDs and methods are proposed in the '107 patent that are based on this understanding of HRV and the association of electrical alternans with mechanical alternans in patient's hearts that are susceptible of tachyarrhythmias.

A pacing system is proposed in the above-referenced '107 patent that would periodically pace to overdrive the heart at a slightly varying and random beat-to-beat pacing rate for short time periods to mimic natural HRV. It is also suggested that a measure of cardiac stability, which can be either a measure of electrical alternans or a measure of blood pressure alternans, be developed from the EGM or a blood pressure sensor, respectively, and that the HRV inducing string of pacing pulses can be modified when either measure is present. It is generally suggested that such measure(s) could be employed to either trigger or inhibit or modify the delivery of the pacing pulses to induce HRV. However, no specific examples are provided as to how the intervals between delivered pacing pulses would actually be modified in the presence of either or both of measured electrical alternans and blood pressure alternans or in the absence of both.

A further method is proposed in the above-referenced '107 patent to simply monitor electrical alternans from the EGM and blood pressure alternans from blood pressure measurements in order to assess cardiac electrical stability from both, particularly to identify a heart state susceptible to tachyarrhythmias. The '107 patent does not set forth any explanation of how the cardiac electrical stability is assessed. However, it appears from the reliance upon the Clancy et al. article and the express description that cardiac instability indicating susceptibility to a tachyarrhythmia would be declared when both electrical alternans and blood pressure alternans are simultaneously present.

Thus, a need continues to exist for an IMD that can be programmed to collect meaningful blood pressure data evidencing a mechanical malfunction of the heart, particularly MPA, associated with HF. A need continues to exist for such an IMD that accumulates event data that can be assessed within the implantable monitor stimulator, or an external medical device that the data is transmitted to, to develop a current indicia of the HF state from which the progression of the disease and the assessment of efficacy of prescribed treatment, e.g., programmed parameters of right and left heart pacing, can be assessed.

SUMMARY OF THE INVENTION

In view of the above need, the present invention provides a system and method for detecting MPA as well as associated MPA episode data and processing the MPA episode data together with MPA episode trend data within an IMD to provide indicia related to the mechanical performance of the HF patient's heart so that the response of the heart to drug or electrical stimulation therapies prescribed to reduce HF symptoms can be assessed.

In accordance with this invention, it is proposed that a HF patient with normal or abnormal cardiac electrical activation sequences may have spontaneous, intermittent, MPA episodes that may not be accompanied by electrical alternans if the contractile processes (calcium cycling and actin-myosin coupling) of the individual myocardial fibers are impaired. Impaired contractile processes can produce beat-to-beat alternating pressure amplitudes despite the normal spread of electrical activity (hence, no electrical alternans).

The present invention is based on the premise that certain MPA characteristics of an MPA episode can be used alone or as a group as a diagnostic marker of HF state. In one embodiment, an MPA episode data set is collected upon satisfaction of MPA detection criteria. The MPA episode data set can be stored in memory associated with a time and date stamp. The MPA characteristics of each MPA episode data set in a series of MPA episode data sets collected over time can be compared or plotted to determine if a trend indicative of change in HF state is discernible.

The MPA episode data points of an MPA episode can comprise one or more of the current number of MPA episodes per unit time, the MPA episode duration, the heart rate at MPA onset and/or MPA end, and various values of the MPA magnitude. The MPA magnitude comprises the difference between the systolic peak blood pressures of two heartbeats. The MPA magnitude data point may be the average or mean MPA magnitude or the maximal MPA magnitude. In certain cases, MPA episodes are marked by a gradual onset and recovery. It is presumed that the time course of the onset and recovery of the MPA may be indicative of the severity of the HF state. Therefore, the MPA magnitudes of an MPA data set accumulated prior to and following declaration of MPA onset may be compared to determine an MPA rate of change or slope at MPA onset. The MPA magnitudes of an MPA data set accumulated prior to and following declaration of MPA end may be compared to determine an MPA rate of change or slope at MPA end. The MPA characteristics of a series of MPA episode data sets can be compared. Changes in one or more of such MPA characteristics can be assessed to determine if the HF state is deteriorating, improving, or staying substantially the same over time.

For example, the heart rate at detection of MPA (i.e., the MPA onset heart rate) is stored for each of "N" stored MPA episodes. The N MPA onset heart rates can be compared to develop an MPA onset heart rate trend. If the MPA heart rate trend shows a heart rate increase or decrease or remain substantially constant over time, then it may be assumed that the HF state is deteriorating, improving or remaining stable. Similarly, an increase in frequency of MPA episodes, the durations of the MPA episodes, and one or more of the above-described MPA magnitudes, can demonstrate that the HF state is deteriorating. A decrease in frequency of MPA episodes, the durations of the MPA episodes, and the MPA magnitude(s) can demonstrate that the HF state is improving.

The present invention is preferably implemented in an implantable monitor capable of measuring the EGM of the heart and a mechanical performance parameter of the heart measured by a blood pressure sensor in the right or left ventricles or by trans-cardiac strain gauges, impedance sensors or sonomicrometers, or by blood flow sensors, motion sensors, force sensors, e.g., accelerometers measuring contraction strength, etc. In one example of the practice of the present invention, the above-identified Chronicle® IHM and pressure sensing lead can be implanted in a HF patient to measure the EGM to determine heart rate and to measure systolic blood pressure. Advantageously, it is not necessary to measure atmospheric pressure to derive absolute pressure measurements in the practice of the present invention, but such absolute pressure data can also be collected if desired. In accordance with the present invention, an algorithm is incorporated to detect the onset and end of MPA episodes.

The MPA episode data points accumulated by the operating algorithm of the IHM are then determined. The IHM would preferably be capable of initiating telemetry transmissions of MPA episode data points to an external medical device. Preferably, the external medical device (or the IHM) would be capable of initiating data transfers to medical care providers of such trend data so that the HF state can be assessed to initiate any appropriate changes in monitoring and/or therapy delivery to the patient.

As described above, the MPA episode data points would be quantified and stored as an intermittent or continuous diagnostic variable within the IHM. Alternatively, it is envisaged that the MPA episode data points would be quantified and stored as an intermittent or continuous diagnostic variable within a therapy delivery IMD, e.g., an implantable pacemaker or drug delivery device. For example, the system of the present invention could be an integrated component to a drug delivery system (implanted or external) and used to manually or automatically determine the dose, frequency and duration of therapeutic drug delivery. Alternatively, and in the preferred embodiment of this device, the system would be part of a cardiac stimulation device capable of delivery of present and emerging electrical therapies to the heart such as pacing, resynchronization, defibrillation, or other stimulation such as PESP stimulation. By example, the increased occurrence of MPA may signal worsening of the cardiac function and may signal an implanted defibrillator that the patient's risk of an dangerous arrhythmia is increased and that the logic for detecting the arrhythmia and/or deciding on the sequence of tiered conversion therapies could be altered to increase the probability of successful detection and treatment. If the IMD provides a pacing function, the heart's response to the applied pacing regimen can be assessed from the magnitude, timing and duration of MPA episodes.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. An embodiment of the invention is disclosed in detail in the context of an exemplary IMD that is modified to accumulate MPA episode data points that are characteristic of the MPA episodes that can be employed to assess HF state of a patient's heart employing one or more sensor for detecting mechanical heart function in operative relation to one or more heart chamber. This illustrated embodiment of the invention is embodied in an IHM but can be incorporated into therapy delivery IMDs as noted above, e.g., an AV sequential, bi-atrial and bi-ventricular, pacing system operating in demand, atrial tracking, and triggered pacing for restoring synchrony in depolarizations and contraction of left and right ventricles in synchronization with atrial sensed and paced events for treating HF and/or bradycardia. The embodiments of the invention can therefore comprise multi-chamber pacing systems programmable to operate as a two, three or four channel pacing system having an AV synchronous operating mode for restoring upper and lower heart chamber synchronization and right and left atrial and/or ventricular chamber depolarization synchrony.

It will be appreciated from the following description that an IMD incorporating the present invention may be utilized to obtain the aforementioned parameters as stored patient data over a period of time. The treating physician is able to initiate uplink telemetry of the patient data in order to review it to make an assessment of the HF state of the patient's heart. The physician can then determine whether a particular therapy is appropriate, prescribe the therapy for a period of time while again accumulating the stored patient data for a later review and assessment to determine whether the applied therapy is beneficial or not, thereby enabling periodic changes in therapy, if appropriate. Such therapies include drug therapies and electrical stimulation therapies, including PESP stimulation, and pacing therapies including single chamber, dual chamber and multi-chamber (bi-atrial and/or bi-ventricular) pacing. Moreover, in patients prone to malignant tachyarrhythmias, the assessment of HF state can be taken into account in setting parameters of detection or classification of tachyarrhythmias and the therapies that are delivered.

Figure 1:
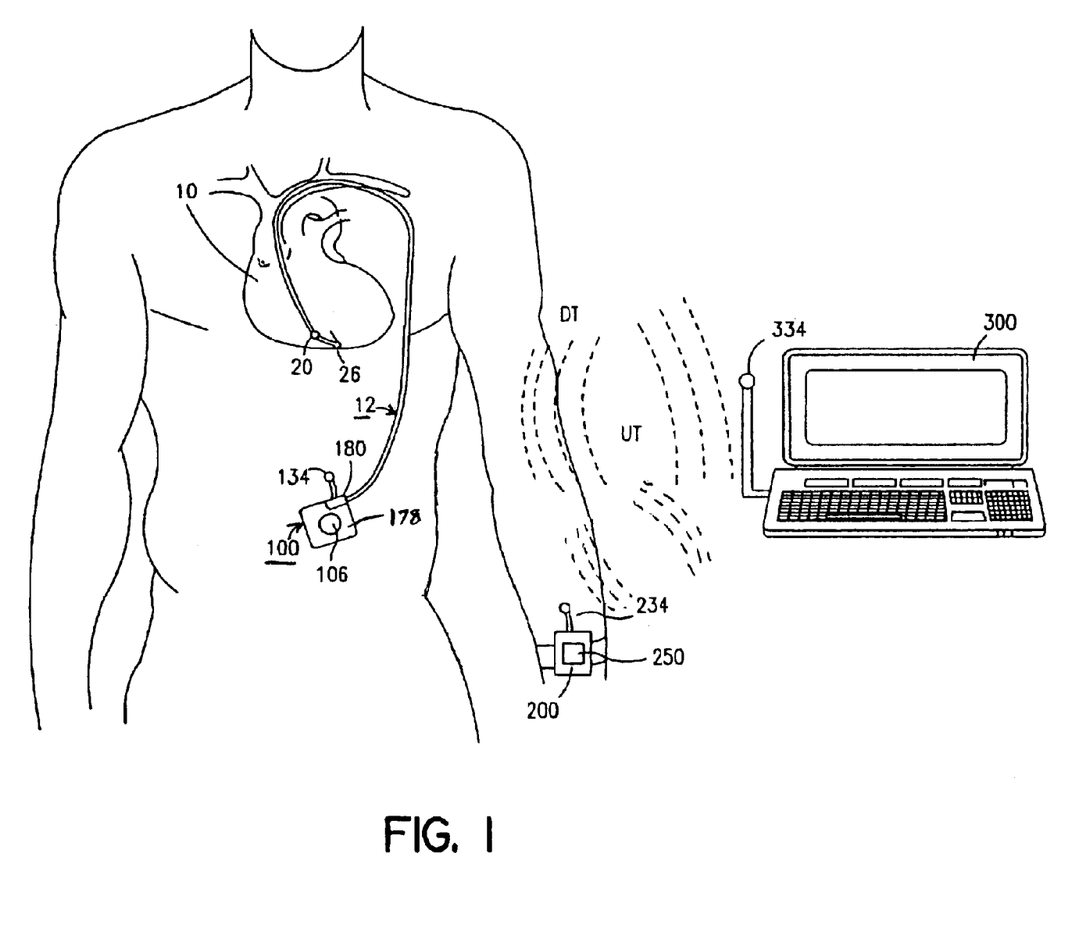
FIG. 1 is a schematic diagram of an exemplary system in which the present invention is preferably implemented.

FIG. 1 schematically illustrates a system that can advantageously be employed in monitoring MPA and collecting and processing MPA episode data in accordance with the teachings of the present invention. Not all of the components or functions of the depicted exemplary system are necessarily employed in the practice of the present invention as described further below.

Figure 2:
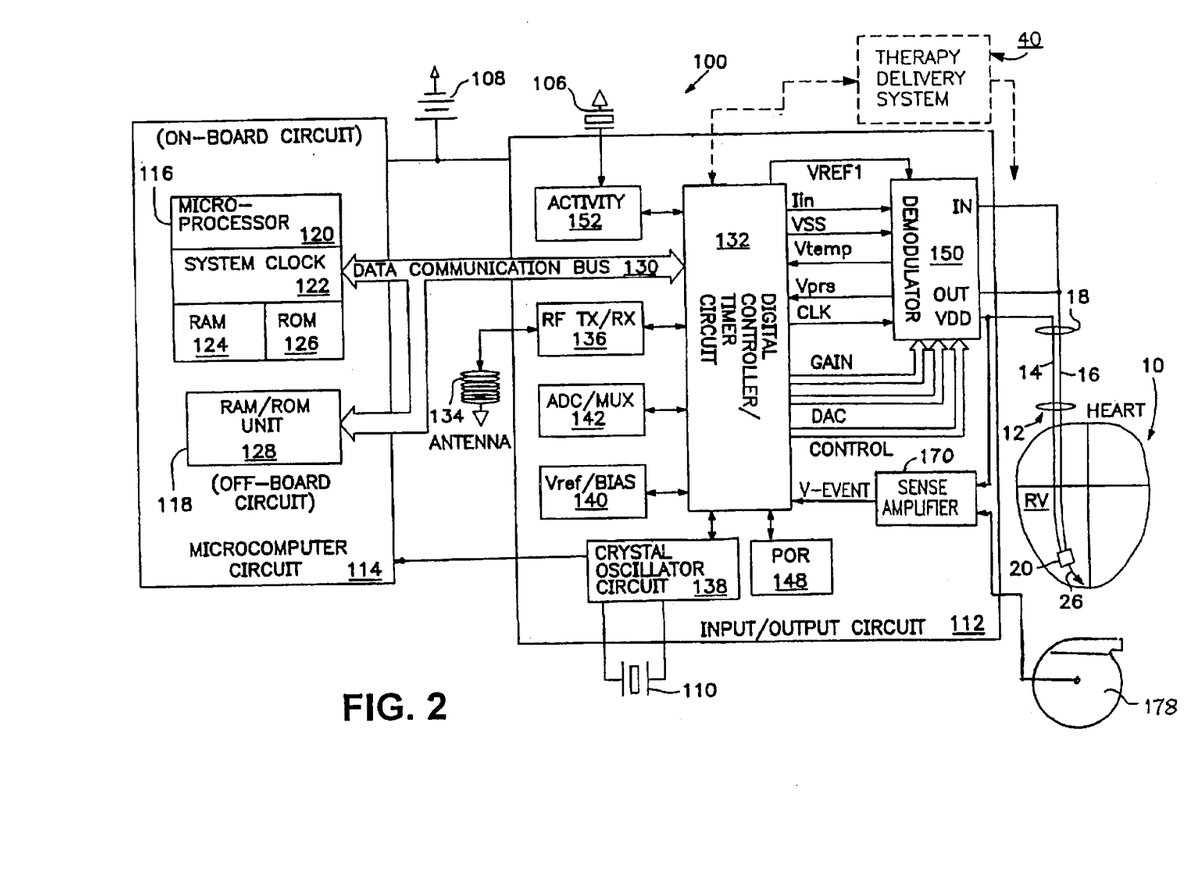
FIG. 2 is a simplified block diagram of one embodiment of IMD circuitry and associated leads employed in the system of FIG. 1 enabling monitoring of MPA from ventricular blood pressure in accordance with the present invention.

The exemplary system illustrated in FIGS. 1 and 2 comprises an exemplary IMD 100 and blood pressure lead 12 locating a blood pressure sensor 20 within the right ventricle near the outflow tract of the patient's heart 10. The exemplary system further comprises an externally worn or otherwise carried atmospheric pressure reference monitor 200 to record contemporaneous atmospheric pressure values, and an external programmer 300. External programmer 300 is used to communicate with the IMD 100 and the atmospheric pressure reference monitor 200 in order to program the operating modes and parameters of IMD 100 or interrogate the data stored in memory of the IMD 100 and atmospheric pressure reference monitor 200.

The IMD 100 preferably comprises the above-referenced Medtronic® CHRONICLE® Model 9520 IHM having the capabilities of deriving and storing the above-referenced pressure data as well as heart rate data from the sensed ventricular EGM and patient activity level as monitored by an activity sensor 106. The pressure sensor lead 12 preferably comprises the above-referenced Model 4328A pressure sensor lead that senses blood pressure using a pressure sensing transducer 20 of the type disclosed in commonly assigned U.S. Pat. No. 5,564,434. The pressure sensor lead 12 also incorporates a distal EGM sense electrode 26 and conventional soft pliant tines that provide passive fixation of the sense electrode 26 in the right ventricle in a manner well known in the art. The proximal connector assembly of pressure sensor lead 12 is configured in conformance with IS-1 standards for bipolar pacing leads and is fitted into a conforming bore of the connector 180 of IMD 100 in the conventional manner. It will be understood that other possible configurations of the IMD 100 can provide cardioversion/defibrillation and/or pacing therapies requiring additional implantable cardiac leads and electrodes preferably for synchronously pacing upper and lower and right and left heart chambers for improving cardiac output in patients suffering from HF.

The CHRONICLE® Model 9520 IHM measures absolute blood pressure, and so the patient is also provided with the atmospheric pressure reference monitor 200, e.g., the above-referenced Medtronic® Model No. 2955HF atmospheric pressure reference monitor. Atmospheric pressure reference monitor 200 is schematically depicted as worn on the patient's wrist, optionally including a timepiece function 250, but it may take other portable configurations so that it can accompany the patient in the patient's daily routine. The functions of an exemplary atmospheric pressure reference monitor 200 in relation to the IHM 100 and programmer 300 are disclosed in commonly assigned U.S. Pat. No. 5,904,708.

Uplink telemetry (UT) and downlink telemetry (DT) transmissions between an RF telemetry antenna 134 of the IMD 100 (schematically illustrated as extending from the connector 180 of the IMD 100) and a telemetry antenna 334 of the external programmer 300 are schematically illustrated in FIG. 1. Similarly, UT and DT transmissions between an RF telemetry antenna 234 of the atmospheric pressure reference monitor 200 and the telemetry antenna 334 of the external programmer 300 are also illustrated in FIG. 1. It will be understood that a direct cable or plug-in connection can be made between ports of the atmospheric pressure reference monitor 200 and the external programmer 300 instead of employing the depicted UT and DT transmissions between the RF telemetry antennas 234 and 334 when atmospheric pressure data is to be read from memory in the atmospheric pressure reference monitor 200. The RF telemetry system preferably operates at a long range of about 2 meters or more in a relatively high frequency range. For convenience of description, the preferred embodiment is described as follows using long range RF telemetry transmission, but the invention and following claims are not be interpreted as so limited. Similarly, the terms "telemeter", "telemetry transmission" and the like are intended to embrace any such action and manner of conveying data and commands between the IMD 100, the atmospheric pressure reference monitor 200, and the external programmer 300 or other monitoring device.

In conventional use of the depicted system, the storage of absolute blood pressure data and ambient pressure data continues for a period of days and the data is periodically transmitted to the external programmer 300 during a telemetry session initiated by medical personnel operating the external programmer 300. The ambient pressure is employed to correct the absolute pressure data.

However, the absolute pressure data that is processed in accordance with the present invention to assess HF state from MPA episode data does not require such correction. The present invention is preferably implemented in a system as depicted in FIGS. 1 and 2 operating in accordance with the flow charts of FIGS. 3–7 to monitor and assess HF state from MPA episode data accumulated from beat-to-beat blood pressure samples and associated data without use of the ambient pressure data. In the case where the IMD 100 is an implantable therapy delivery device, the assessment of MPA can be employed to assess efficacy of the delivered therapy.

FIG. 2 is a simplified block diagram of the pressure sensing lead 12 and IMD 100 in relation to patient's heart 10. The lead 12 has first and second lead conductors 14 and 16 extending from the connector 180 to the blood pressure sensor 20 disposed near the distal fixation mechanism 26 and to the distal tip sense electrode 26. The blood pressure sensor 20 preferably includes a variable pickoff capacitor and a fixed reference capacitor and signal modulating circuit described in detail in the above-referenced '434 patent that develops both blood pressure and temperature time-modulated intervals that are decoded as blood pressure and temperature signal values in demodulator 150. The proximal end of lead 12 is formed as a conventional bipolar, in-line pacing lead connector and is coupled to the monitor connector 180 which is formed as a conventional bipolar in-line pacemaker pulse generator connector block assembly.

The circuitry of IMD 100 is powered by battery 108 and generally comprises a microcomputer 114 coupled through data communication bus 130 with an input/output circuit 112 that is coupled to the activity sensor 106, the telemetry antenna 134, the lead conductors 14, 16, and a crystal 110. The input/output circuit 112 includes the digital controller/timer circuit 132 and the associated components including the crystal oscillator 138, power-on-reset (POR) circuit 148, Vref/BIAS circuit 140, ADC/MUX circuit 142, RF transmitter/receiver circuit 136, optional activity circuit 152 and pressure signal demodulator 150.

Crystal oscillator circuit 138 and crystal 110 provide the basic timing clock for the digital controller/timer circuit 132. Vref/BIAS circuit 140 generates stable voltage reference Vref and current levels from battery 108 for the circuits within the digital controller/timer circuit 132, and the other identified circuits including microcomputer 114 and demodulator 150. Power-on-reset circuit 148 responds to initial connection of the circuitry to the battery 108 for defining an initial operating condition and also resets the operating condition in response to detection of a low battery voltage condition. Analog-to-digital converter (ADC) and multiplexor circuit 142 digitizes analog signals Vprs and Vtemp received by digital controller/timer circuit 132 from demodulator 150 for storage by microcomputer 114.

Data signals transmitted out through RF transmitter/receiver circuit 136 during telemetry are multiplexed by ADC/MUX circuit 142. Voltage reference and bias circuit 140, ADC/MUX circuit 142, POR circuit 148, crystal oscillator circuit 138 and optional activity circuit 152 may correspond to any of those presently used in currently marketed, implantable cardiac pacemakers.

The digital controller/timer circuit 132 includes a set of timers and associated logic circuits connected with the microcomputer 114 through the data communications bus 130. Microcomputer 114 contains an on-board chip including microprocessor 120, associated system clock 122, and on-board RAM and ROM chips 124 and 126, respectively. In addition, microcomputer 114 includes an off-board circuit 118 including separate RAM/ROM chip 128 to provide additional memory capacity. Microprocessor 120 is interrupt driven, operating in a reduced power consumption mode normally, and awakened in response to defined interrupt events, which may include the periodic timing out of data sampling intervals for storage of monitored data, the transfer of triggering and data signals on the bus 130 and the receipt of programming signals. A real-time clock and calendar function may also be included to correlate stored data to time and date.

Microcomputer 114 controls the operating functions of digital controller/timer 132, specifying which timing intervals are employed, and controlling the duration of the various timing intervals, via the bus 130. The specific current operating modes and interval values are programmable. The programmed-in parameter values and operating modes are received through the antenna 134, demodulated in the RF transmitter/receiver circuit 136 and stored in RAM/ROM chip 128.

Data transmission to and from the external programmer 300 of FIG. 1 is accomplished by means of the telemetry antenna 134 and the associated RF transmitter and receiver 136, which serves both to demodulate received DT transmissions and to UT transmit data to the external programmer 300. A number of power, timing and control signals described in greater detail in the above-referenced '434 patent are supplied by the digital controller/timer circuit 132 to the demodulator 150 to initiate and power the operation of the blood pressure sensor 20 and selectively read out the pressure and temperature signals Vprs and Vtemp. An active lead conductor 16 is attached through the connector block terminals to input and output terminals of demodulator 150 that supplies a voltage VREG at the output terminal. A passive lead conductor 14 is coupled through to the VDD supply terminal of the demodulator 150. The voltage signals Vprs and Vtemp developed from intervals between current pulses received at the input terminal are provided by demodulator 150 to the digital controller/timer circuit 132. The voltage signals Vprs and Vtemp are converted to binary data in an ADC/MUX circuit 142 and stored in RAM/ROM chip 128 in a manner well known in the art.

The IMD 100 functions as an implantable physiologic signal sensor, specifically for monitoring and storing digitized blood pressure and temperature from the absolute pressure and temperature sensor 20 as well as patient activity and EGM data as described below. The EGM of the heart, particularly the R-wave of the PQRST complex, is sensed between the active distal tip electrode 26 and the indifferent electrode formed by the hermetically sealed housing or can 178 of IMD 100 by sense amplifier 170 in a conventional unipolar sensing configuration. The sense amplifier 170 declares a V-EVENT when the R-wave is sensed, and the V-EVENT is supplied to the digital controller/timer circuit 132 and functions as an interrupt to the microprocessor 120 in a manner well known in the art.

FIG. 2 also shows the configuration of a therapy delivery device by inclusion of the therapy delivery system block 40 shown in broken lines. The particular therapy delivery system 40 may include one or more of the systems described above.

In accordance with the present invention, the IMD 100 periodically stores digitized MPA blood pressure data from sampled blood pressure and certain heart rate data as MPA characteristics when MPA detection criteria are met. Other data, e.g., patient activity level and date and time can also be stored in association with the MPA characteristics as MPA episode data in RAM. Trend data can be derived from comparison of MPA episode data points of a series of MPA episodes in IHM 100. Or, the MPA trend data can be determined in the programmer 300 or a more remote data processing center receiving UT transmissions of the MPA episode data sets from the IHM 100 in real time or after temporary storage in RAM of the IHM 100. A patient alert or a notification to the physician can be initiated if the trend indicates deterioration of the HF state.

Figure 6:
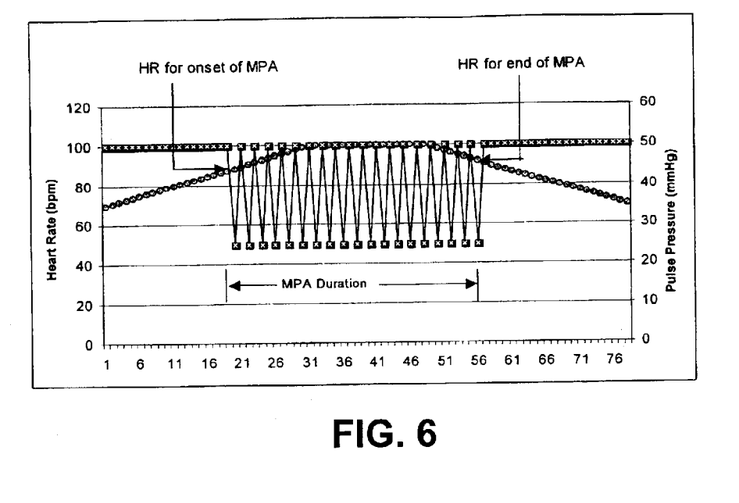
FIG. 6 is a graphical schematic depiction of such an MPA episode.

The MPA episode data points can comprise one or more of the frequency of MPA episodes per unit time, the duration of each MPA episode, the heart rate at onset and/or termination of each MPA episode, the average or mean heart rate of the MPA episode, and the magnitude of the MPA. The MPA magnitude comprises the difference between the systolic peak blood pressures of at least two successive heartbeats. The MPA magnitude data point may be that MPA magnitude measured at onset or as an average or mean MPA magnitude or the maximal change in the MPA magnitude of all MPA magnitudes measured during the MPA episode. In certain cases, MPA episodes are marked by a gradual onset and recovery. It is presumed that the time course of the onset and recovery of the MPA may be indicative of the severity of the HF state. Therefore, the MPA magnitudes of an MPA episode data set may be compared to determine an MPA rate of change from detection of onset to a maximal MPA magnitude and then from the maximal MPA magnitude until recovery. The MPA rate of change during an onset phase and/or during a recovery phase can comprise an MPA episode data point of the MPA episode data set. Changes in one or more of such MPA episode data points can be assessed to determine if the HF state is deteriorating, improving, or staying substantially the same over time. FIG. 6 is a graphical schematic depiction of such an MPA episode marked by the alternating high and low peak pressures and showing the MPA duration extending from MPA onset to MPA end. The associated heart rate is also depicted in FIG. 6 as increasing at MPA onset and decreasing at MPA end.

Figure 3:
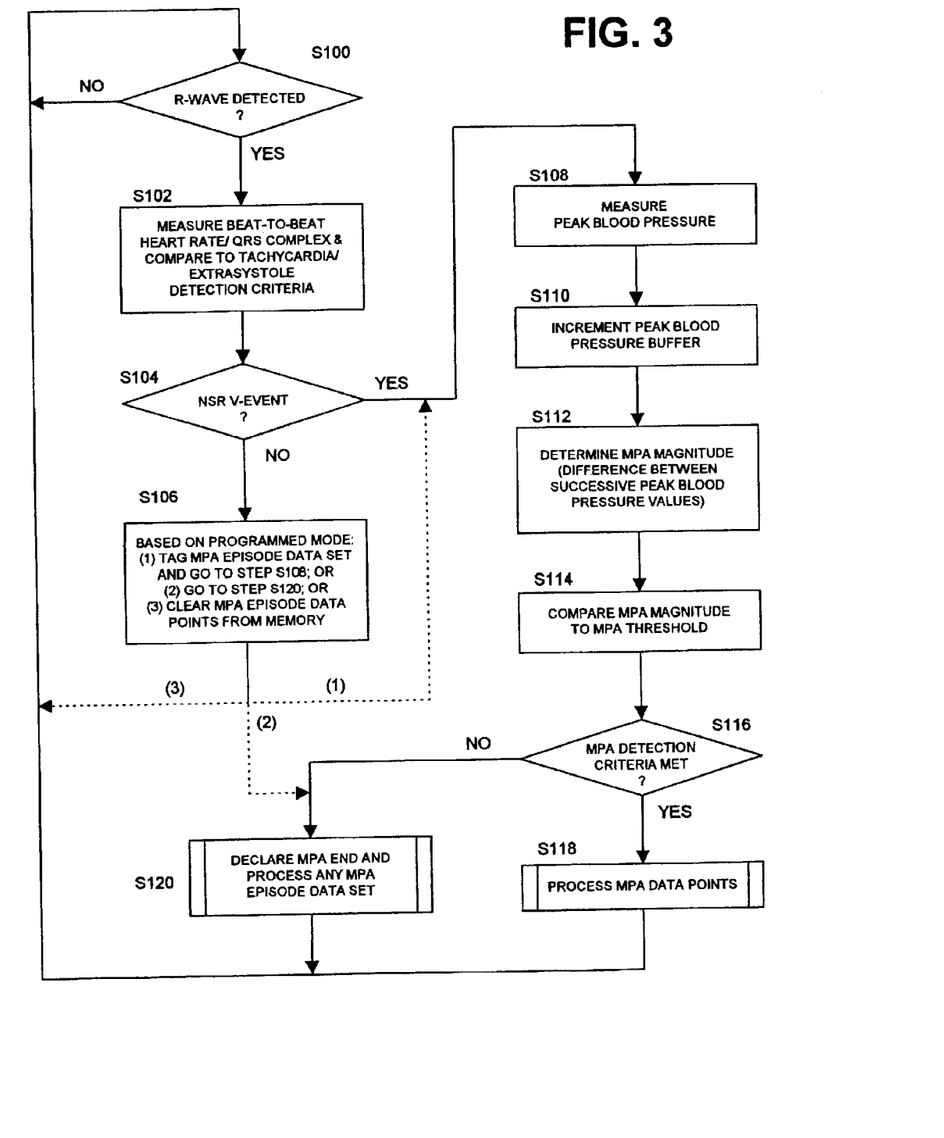
FIG. 3 is a top level flowchart of the detection of MPA episodes and the collection and processing of blood pressure data and associated event data during the MPA episode that can be stored in IMD memory or employed to trigger or alter a pacing therapy.

The collection of such MPA episode data points of an MPA episode is illustrated in FIG. 3. Steps S100–S106 relate to detection of a normal sinus rhythm (NSR) R-wave resulting in a V-EVENT in FIG. 2, and steps S108–S118 relate to the initial and continued detection of an MPA episode. It will be understood that the particular order of these steps of FIG. 3 may be changed from the depicted order. For example, collection of blood pressure data and detection of MPA during successive heart cycles can precede determination that the heart is in NSR.

It is known that MPA that might not otherwise be present when the heart exhibits NSR can be observed following ectopic R-waves (extrasystoles) or during tachycardia episodes. MPA data collected under such circumstances may not be a reliable or useful indicator of HF state. At least the MPA data should be identified as associated with an extrasystole or collected during a tachycardia episode. In step S102, the beat-to-beat interval or heart rate is determined each time that an R-wave (V-EVENT) is detected for comparison to a tachycardia interval or heart rate. Optionally, the QRS complex width can be measured and compared to a width threshold or morphology template characteristic of either the wider QRS complex or the narrower normal QRS complex. The thresholds and the comparisons to be employed can be programmed by the physician in step S100. Therefore, a determination is made in step S102 whether or not the last V-EVENT signifies an extrasystole or a tachycardia depending upon the results of the comparison of the beat-to-beat interval to the tachycardia threshold and/or by comparison of QRS complex to the QRS threshold If the results of the comparison in step S104 indicate NSR, then the steps S108–S120 are followed. If the results of the comparison in step S104 do not indicate NSR, then the event is tagged as "not NSR" and the steps S108–S120 are followed. However, the physician may program the IMD to respond in other ways. For example, in certain cases, the extrasystole or tachycardia may occur during a previously detected MPA episode. In such a case, it may be desirable in step S106 to terminate MPA data processing in step S118 as described below and ignore the accumulated MPA data set. Or, the physician may program step S106 to declare the MPA episode terminated and process the MPA episode data set in step S120 in the manner described below.

The blood pressure samples over the heart cycle are made in step S108 and stored in a temporary buffer in step S110. The process repeats for each successive V-EVENT, and succeeding sampled peak blood pressure values are subtracted from one another and stored temporarily in a buffer on a FIFO basis in step S112. Each determined pressure difference is immediately compared to a programmed MPA threshold in step S114. The onset, the continuation, and the end of an MPA episode are declared in step S116 as a result of each such comparison made in step S114. It will be understood that the MPA threshold used in step S114 resulting in a declaration of onset of an MPA episode may be different from the MPA threshold used in step S114 after an MPA episode is declared to determine if the MPA episode is continuing or has ended. It will also be understood that a number of the pressure difference data stored in the buffer preceding declaration of onset and following declaration of MPA episode end may be used in succeeding steps S118 and S120.

The processing of MPA episode data points is commenced in step S118 (depicted in FIG. 4) and continues for the duration of the MPA episode. The MPA episode may be terminated either by a subsequent failure to detect MPA in step S116 or in response to an ectopic or tachycardia V-EVENT depending upon how such V-EVENTS are treated in step S106. First, it is determined whether the current detection of MPA in step S116 is the first one or is a continuing MPA detection during an earlier declared MPA episode by checking the MPA status flag in step S122.

Figures 4, 5:
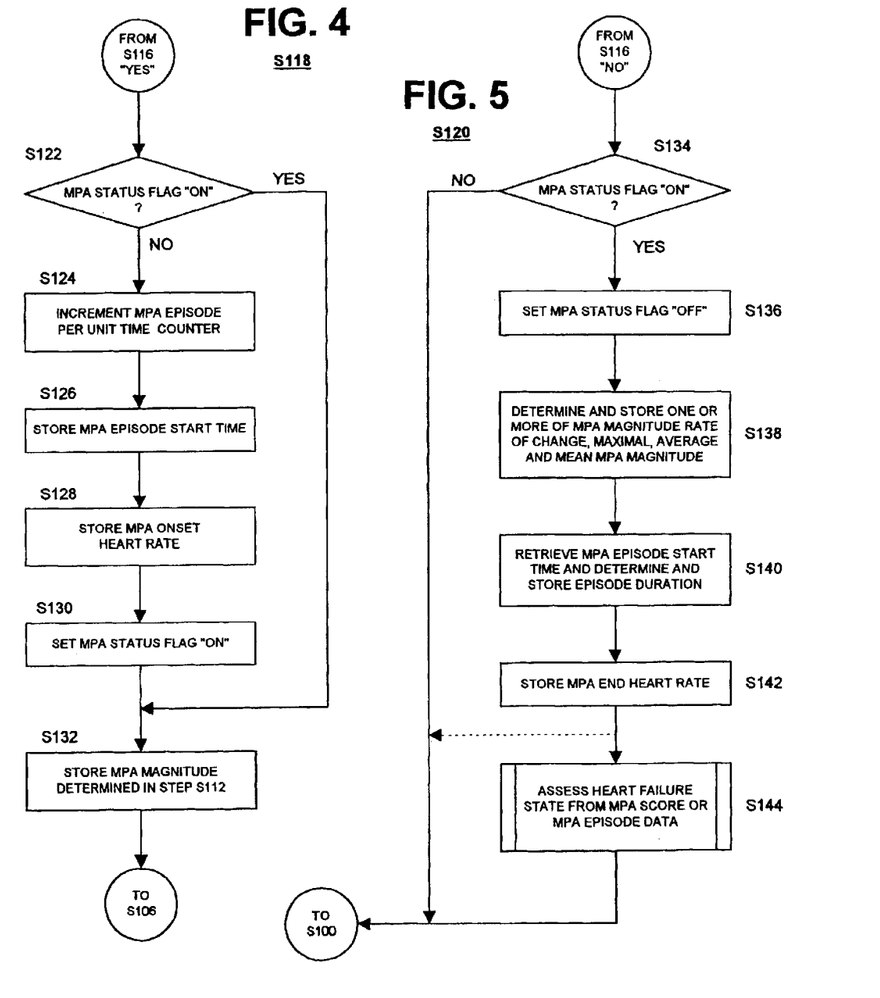
FIG. 4 is a detailed flowchart of step S118 of FIG. 3.
FIG. 5 is a detailed flowchart of step S120 of FIG. 3.

If the MPA detection has just been declared in step S116, then the MPA status flag is determined to not be ON in step S122, and steps S124–S130 are performed to establish certain MPA characteristics of the newly detected MPA episode. An MPA episode count per unit of time, e.g., 24 hours, is incremented in step S124, and the MPA episode start time is stored in step S126. The MPA onset heart rate and the MPA magnitudes of a certain number of heart cycles preceding detection of MPA onset stored in step S112 are frozen in the buffer or transferred to a further buffer for processing as described further below. Then, the MPA status flag is set ON in step S130, and the MPA magnitude determined in step S112 is stored in step S132.

Steps S124–S130 are then bypassed at step S122 each time that a succeeding MPA magnitude continues to meet the MPA detection criteria in step S118. In this way, the MPA data points comprising the MPA episode count and the MPA onset heart rate are established for the current MPA episode, and MPA magnitudes are accumulated for the duration of the MPA episode to determine one or more of average, mean, and maximal MPA magnitude data points for the MPA episode.

The process of steps S100–S132 repeats until the MPA detection criteria are not met and the MPA episode end is declared in step S116. An MPA episode data set is accumulated, by the point in time that the MPA episode end is declared, that includes the MPA episode start time, the stored MPA magnitudes, and the MPA episode data points comprising the MPA episode count and the MPA onset heart rate for the current MPA episode. In step S120, depicted in FIG. 5, the MPA episode data set is completed and further processes are completed, if programmed ON, to assist in assessing the HF state.

First, the MPA status flag is checked in step S134 and is turned OFF in step S136 if the MPA status flag is set ON, as would have been done in step S130 for the current MPA episode. The bypass from step S134 is simply provided to return to step S100 in heart cycles when an MPA episode onset is not declared in step S116.

In step S138, the stored MPA magnitudes of the concluded MPA episode are retrieved and processed to provide further MPA episode MPA magnitude data points that are stored with the MPA episode data set. In step S140, the MPA duration data point is determined from the MPA end time and the stored MPA start time and stored. In step S142, the MPA end heart rate data point is determined and stored. The completed MPA episode data set can be stored in IMD memory or UT transmitted to an external programmer 300, for example. The completed MPA episode data set can be further processed in step S144 to derive an assessment of HF state for use in adjusting therapies, if necessary. Step S144 can be performed either in the IMD 100 or in the external programmer 300 or in remote processing equipment remote from programmer 300 and IMD 100 or in a collaboration of the IMD 100, the external programmer 300 and the remote processing equipment.

The determination of the MPA magnitude data point(s) in step S138 can be selectively programmed to include one or more of determination of: (1) the MPA magnitude rate of change at MPA onset; (2) the MPA magnitude rate of change at MPA end; (3) the maximal MPA magnitude; (4) the mean MPA magnitude; and (5) the average MPA magnitude. The MPA magnitude rate of change data point at MPA onset can be determined comparing the change in MPA magnitudes of set numbers of MPA magnitudes stored prior to and following MPA onset. Similarly, the MPA magnitude rate of change data point at MPA off can be determined comparing the change in MPA magnitudes of set numbers of MPA magnitudes stored prior to and following declaration of MPA end.

Figure 7:
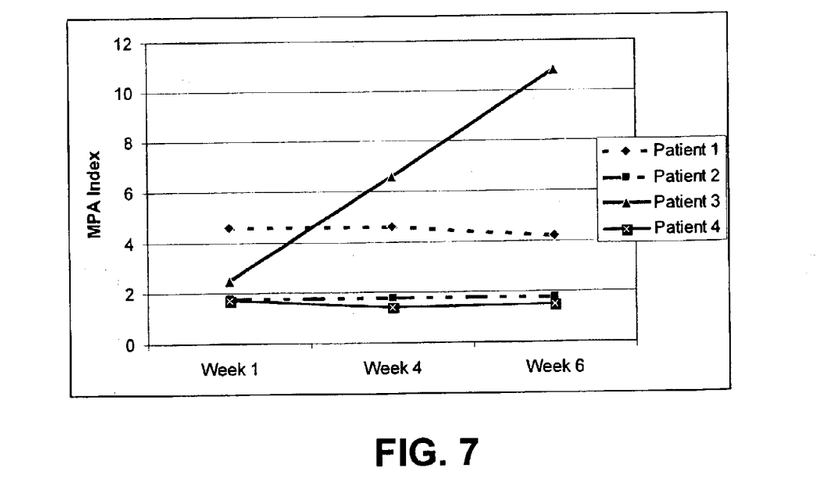
FIG. 7 is a graphical depiction MPA characteristic trends manifested by HF patient MPA episode data sets accumulated over time from four patients.

FIG. 7 is a graphical depiction one specific measure of the frequency of MPA, the "MPA Index", showing characteristic trends manifested by four HF patients. MPA episode data sets accumulated over time from acute readings of four patients having an IMD of the type described above implanted. Data were collected at 2–3 week intervals. It is noted that three patients had stable values for MPA Index over time, and they were medically stable over the same time interval. However, one patient, patient #3, had an increasing MPA Index at each study period and then, after week X, had a worsening heart failure episode requiring hospitalization and intensive intervention.

Thus, it is demonstrated MPA episodes can be detected and that MPA characteristics of the MPA episode can be used alone or as a group as a diagnostic marker of HF state. The MPA episode data set can be stored in memory associated with a time and date stamp. The MPA characteristics of each MPA data set in a series of MPA data sets collected over time can be compared or plotted to determine if a trend indicative of change in HF state is discernible.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

What is claimed is:

1. A method of operation of an implantable heart monitor implanted in a patient's body having electrogram (EGM) sense electrodes coupled with EGM sense circuitry to generate sense events upon detection of cardiac depolarizations and a blood pressure measurement transducer disposed in a heart chamber and coupled with blood pressure measurement circuitry to assess heart failure state as a function of mechanical pulsus alternans (MPA) comprising:

operating the blood pressure measurement transducer to make blood pressure measurements;

detecting the onset of an MPA episode of the patient's heart from the blood pressure measurements;

determining at least one MPA characteristic of the MPA episode; and assessing heart failure state from the MPA characteristic.

2. The method of claim 1, wherein the step of determining the at least one MPA characteristic further comprises determining an MPA onset heart rate associated with the detection of onset of the MPA episode.

3. The method of claim 2, wherein the assessing step further comprises comparing a series of stored MPA onset heart rates to determine if the stored MPA onset heart rates exhibit an increasing heart rate trend signifying an improving heart failure state, a decreasing heart rate trend signifying a deteriorating heart failure state or a substantially unchanging heart rate trend signifying a stable heart failure state.

4. The method of claim 1, further comprising the step of detecting the end of an MPA episode of the patient's heart from the blood pressure measurements, and wherein the step of determining the at least one MPA characteristic further comprises determining an MPA end heart rate associated with the detection of the end of the MPA episode.

5. The method of claim 4, wherein the assessing step further comprises comparing a series of stored MPA end heart rates to determine if the stored MPA end heart rates exhibit an increasing heart rate trend signifying an improving heart failure state, a decreasing heart rate trend signifying a deteriorating heart failure state or a substantially unchanging heart rate trend signifying a stable heart failure state.

6. The method of claim 1, wherein the step of determining the MPA characteristic further comprises:

determining the differences between the systolic peak blood pressures of two heart beats as MPA magnitudes; and determining a maximal MPA magnitude data point from the determined MPA magnitudes.

7. The method of claim 6, wherein the assessing step further comprises comparing a series of stored maximal MPA magnitude data points to determine if the stored maximal MPA magnitude data points exhibit a decreasing MPA magnitude trend signifying an improving heart failure state, an increasing MPA magnitude trend signifying a deteriorating heart failure state or a substantially unchanging MPA magnitude trend signifying a stable heart failure state.

8. The method of claim 1, wherein the step of determining the MPA characteristic further comprises:

determining the differences between the systolic peak blood pressures of two heart beats as MPA magnitudes; and determining a mean MPA magnitude data point from the determined MPA magnitudes.

9. The method of claim 8, wherein the assessing step further comprises comparing a series of stored mean MPA magnitude data points to determine if the stored mean MPA magnitude data points exhibit a decreasing MPA magnitude trend signifying an improving heart failure state, an increasing MPA magnitude trend signifying a deteriorating heart failure state or a substantially unchanging MPA magnitude trend signifying a stable heart failure state.

10. The method of claim 1, wherein the step of determining the MPA characteristic further comprises:
determining the differences between the systolic peak blood pressures of two heart beats as MPA magnitudes; and
determining an average MPA magnitude data point from the determined MPA magnitudes.

11. The method of claim 10, wherein the assessing step further comprises comparing a series of stored average MPA magnitude data points to determine if the stored average MPA magnitude data points exhibit a decreasing MPA magnitude trend signifying an improving heart failure state, an increasing MPA magnitude trend signifying a deteriorating heart failure state or a substantially unchanging MPA magnitude trend signifying a stable heart failure state.

12. The method of claim 1, further comprising the step of detecting the end of an MPA episode of the patient's heart from the blood pressure measurements, and wherein the step of determining the MPA characteristic comprises determining an MPA episode duration data point.

13. The method of claim 12, wherein the assessing step further comprises comparing a series of stored MPA duration data points to determine if the stored MPA duration data points exhibit a decreasing MPA duration trend signifying an improving heart failure state, an increasing MPA duration trend signifying a deteriorating heart failure state or a substantially unchanging MPA duration trend signifying a stable heart failure state.

14. The method of claim 1, wherein the step of determining the MPA characteristic further comprises:
determining the differences between the systolic peak blood pressures of two heart beats as MPA magnitudes; and
determining an MPA magnitude rate of change data point from the determined MPA magnitudes.

15. The method of claim 14, wherein the assessing step further comprises comparing a series of stored MPA rate of change data points to determine if the stored MPA rate of change data points exhibit a decreasing MPA rate of change trend signifying an improving heart failure state, an increasing MPA rate of change trend signifying a deteriorating heart failure state or a substantially unchanging MPA rate of change trend signifying a stable heart failure state.

16. A system for operating an implantable heart monitor implanted in a patient's body having electrogram (EGM) sense electrodes coupled with EGM sense circuitry to generate sense events upon detection of cardiac depolarizations and a blood pressure measurement transducer disposed in a heart chamber and coupled with blood pressure measurement circuitry to assess heart failure state as a function of mechanical pulsus alternans (MPA) comprising:
means for operating the blood pressure measurement transducer to make blood pressure measurements;
means for detecting the onset of an MPA episode of the patient's heart from the blood pressure measurements;
means for determining at least one MPA characteristic of the MPA episode suitable for assessing heart failure state.

17. The system of claim 16, wherein the means for determining the at least one MPA characteristic further comprises means for determining an MPA onset heart rate associated with the detection of onset of the MPA episode.

18. The system of claim 17, further comprising means for comparing a series of stored MPA onset heart rates to determine if the stored MPA onset heart rates exhibit an increasing heart rate trend signifying an improving heart failure state, a decreasing heart rate trend signifying a deteriorating heart failure state or a substantially unchanging heart rate trend signifying a stable heart failure state.

19. The system of claim 16, further comprising means for detecting the end of an MPA episode of the patient's heart from the blood pressure measurements, and wherein the means for determining the at least one MPA characteristic further comprises means for determining an MPA end heart rate associated with the detection of the end of the MPA episode.

20. The system of claim 19, further comprising means for comparing a series of stored MPA end heart rates to determine if the stored MPA end heart rates exhibit an increasing heart rate trend signifying an improving heart failure state, a decreasing heart rate trend signifying a deteriorating heart failure state or a substantially unchanging heart rate trend signifying a stable heart failure state.

21. The system of claim 16, wherein the means for determining the MPA characteristic further comprises:
means for determining the differences between the systolic peak blood pressures of two heart beats as MPA magnitudes; and
means for determining a maximal MPA magnitude data point from the determined MPA magnitudes.

22. The system of claim 21, further comprising means for comparing a series of stored maximal MPA magnitude data points to determine if the stored maximal MPA magnitude data points exhibit a decreasing MPA magnitude trend signifying an improving heart failure state, an increasing MPA magnitude trend signifying a deteriorating heart failure state or a substantially unchanging MPA magnitude trend signifying a stable heart failure state.

23. The system of claim 16, wherein the means for determining the MPA characteristic further comprises:
means for determining the differences between the systolic peak blood pressures of two heart beats as MPA magnitudes; and
means for determining a mean MPA magnitude data point from the determined MPA magnitudes.

24. The system of claim 23, further comprising means for comparing a series of stored mean MPA magnitude data points to determine if the stored mean MPA magnitude data points exhibit a decreasing MPA magnitude trend signifying an improving heart failure state, an increasing MPA magnitude trend signifying a deteriorating heart failure state or a substantially unchanging MPA magnitude trend signifying a stable heart failure state.

25. The system of claim 16, wherein the means for determining the MPA characteristic further comprises:
means for determining the differences between the systolic peak blood pressures of two heart beats as MPA magnitudes; and
means for determining an average MPA magnitude data point from the determined MPA magnitudes.

26. The system of claim 25, further comprising means for comparing a series of stored average MPA magnitude data points to determine if the stored average MPA magnitude data points exhibit a decreasing MPA magnitude trend signifying an improving heart failure state, an increasing MPA magnitude trend signifying a deteriorating heart failure state or a substantially unchanging MPA magnitude trend signifying a stable heart failure state.

27. The system of claim 16, further comprising means for detecting the end of an MPA episode of the patient's heart from the blood pressure measurements, and wherein the means for determining the MPA characteristic comprises means for determining an MPA episode duration data point.

28. The system of claim 16, further comprising means for comparing a series of stored MPA duration data points to determine if the stored MPA duration data points exhibit a decreasing MPA duration trend signifying an improving heart failure state, an increasing MPA duration trend signifying a deteriorating heart failure state or a substantially unchanging MPA duration trend signifying a stable heart failure state.

29. The system of claim 16, wherein the means for determining the MPA characteristic further comprises:
   means for determining the differences between the systolic peak blood pressures of two heart beats as MPA magnitudes; and
   means for determining an MPA magnitude rate of change data point from the determined MPA magnitudes.

30. The system of claim 29, further comprising means for comparing a series of stored MPA rate of change data points to determine if the stored MPA rate of change data points exhibit a decreasing MPA rate of change trend signifying an improving heart failure state, an increasing MPA rate of change trend signifying a deteriorating heart failure state, or a substantially unchanging MPA rate of change trend signifying a stable heart failure state.

* * * * *